(12) United States Patent
Yamazaki et al.

(10) Patent No.: US 9,345,863 B2
(45) Date of Patent: May 24, 2016

(54) BENDING OPERATION MEMBER, AND MEDICAL APPARATUS

(71) Applicant: Terumo Kabushiki Kaisha, Tokyo (JP)

(72) Inventors: Ryosuke Yamazaki, Shizuoka (JP); Satoru Suehara, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/219,569

(22) Filed: Mar. 19, 2014

(65) Prior Publication Data

US 2014/0207059 A1 Jul. 24, 2014

Related U.S. Application Data

(63) Continuation of application No. PCT/JP2012/068104, filed on Jul. 17, 2012.

(51) Int. Cl.
*A61M 25/10* (2013.01)
*A61M 25/01* (2006.01)
*A61B 1/005* (2006.01)

(52) U.S. Cl.
CPC .............. *A61M 25/10* (2013.01); *A61B 1/0052* (2013.01); *A61B 1/0057* (2013.01); *A61M 25/0136* (2013.01); *A61M 25/0147* (2013.01); *A61M 25/0138* (2013.01)

(58) Field of Classification Search
CPC .............. A61B 1/0052; A61B 1/0057; A61M 25/0136; A61M 25/0138; A61M 25/0147; A61M 25/10
See application file for complete search history.

(56) References Cited

U.S. PATENT DOCUMENTS

| 2003/0092965 A1* | 5/2003 | Konomura et al. ............ 600/146 |
| 2008/0139886 A1 | 6/2008 | Tatsuyama |
| 2013/0047755 A1* | 2/2013 | Okamoto ........................ 74/89.2 |

FOREIGN PATENT DOCUMENTS

| JP | 2-063476 | 3/1990 |
| JP | 07-080077 | 3/1995 |
| JP | 11-000307 | 1/1999 |
| JP | 2008142199 A | 6/2008 |

OTHER PUBLICATIONS

International Search Report mailed Aug. 14, 2012 in related International Application PCT/JP2012/068104 with English-language translation (4 pgs.).

* cited by examiner

*Primary Examiner* — Imani Hayman
(74) *Attorney, Agent, or Firm* — Foley & Lardner LLP

(57) ABSTRACT

A bending operating member for performing a bending operation on an elongated member having flexibility in a direction intersecting an axial direction of the elongated member, the bending operating member includes a pulling member, at least a portion of the pulling member being configured to be connected to a distal portion of the elongated member such that, when the pulling member is pulled in the axial direction of the elongated member, the pulling member causes the elongated member to bend; a moving member that is connected to the pulling member, the moving member being configured to move so as to pull the pulling member in the axial direction of the elongated member; a rotating member that is operatively connected to the moving member and is rotatable around a longitudinal axis of the elongated member; and a converting part that converts rotation of the rotating member into movement of the moving member.

14 Claims, 7 Drawing Sheets

BENDING OPERATION MEMBER, AND MEDICAL APPARATUS

CROSS-REFERENCE TO RELATED APPLICATIONS

This application is a continuation application filed under 35 U.S.C. 111(a) claiming the benefit under 35 U.S.C. §§120 and 365(c) of PCT International Application No. PCT/JP2012/068104 filed on Jul. 17, 2012, the entire content of which is hereby incorporated by reference in its entirety.

BACKGROUND

1. Technical Field

The present disclosure relates to a bending operating member used for a bending operation of an elongated member having flexibility, and a medical apparatus equipped with the bending operating member.

2. Background Art

In the medical field, an elongated member having flexibility is generally used as medical equipment for access for performing administration of medicine into a living body, suction or injection of various fluids, introduction of a medical device into the living body, or the like. Prior to the introduction of the medical device or the like, this type of elongated member is inserted into a lumen (a blood vessel, a body cavity, or the like) of the living body, and is guided to a target area, such as a part to be treated and its peripheral part. In order to appropriately guide the elongated member to the target area during such use, it is often necessary to introduce the elongated member along a curved path like the lumen of the living body. For this reason, an operating member for a bending operation capable of arbitrarily performing a bending operation by a user's proximal operation when the elongated member is used may be used after being assembled into the elongated member.

JP-A-2008-142199 describes an operating member including an operating wire connected to an elongated member and a handle that winds the operating wire to thereby bend the elongated member, and an endoscope into which the operating member is assembled. In this operating member, the handle is provided to protrude from a side portion of a case installed on a proximal side of the operating member, and the handle is rotated around an axis orthogonal to an axial direction of the elongated member and thereby the operating wire is wound to perform a bending operation.

However, in the operating member described above, the elongated member can be bent, but operational constraints may occur in an apparatus in which the operating member is assembled. For example, if the handle of the operating member is installed at a proximal operating section of the medical device, so that a user is enabled to simply perform a bending operation at hand, the handle is provided at the side portion of the case installed at the operating member so as to protrude therefrom. The user must carefully perform various operations using the proximal operating section so that the handle is not accidentally touched by fingers. For this reason, use of the operating member of the related art results in a medical device that forces excessive caution while in use and has poor user-friendliness.

Thus, there is a need for a bending operating member that can simply perform the bending operation of an elongated member having flexibility and can provide a medical apparatus that has improved operativity and convenience during use, and a medical apparatus equipped with the bending operating member.

SUMMARY OF INVENTION

In one embodiment, a bending operating member capable of performing a bending operation of bending an elongated member having flexibility in a direction intersecting an axial direction is provided. The bending operating member includes a pulling member that has at least a portion connected to a distal portion side of the elongated member and is pulled in the axial direction of the elongated member to thereby bend the elongated member; a moving member that is connected to the pulling member on a proximal portion side of the elongated member and moves in the axial direction of the elongated member to pull the pulling member; a rotating member that is connected to the moving member and is rotatable around the axis of the elongated member; and a converting part that converts the rotation of the rotating member into the movement of the moving member.

In one aspect, the converting part has a groove portion that is formed in the rotating member and extends so as to incline in the axial direction of the elongated member, a sliding member that is arranged at the groove portion and is slidingly movable along the groove portion with the rotation of the rotating member, and a transmission member that transmits the movement of the sliding member to the moving member.

In one aspect, the groove portion is provided with at least a first inclination portion that inclines at a first angle and a second inclination portion that inclines at a second angle different from the first angle.

In one aspect, the groove portion further includes a third inclination portion with a third angle different from the second angle, and the second angle has a larger inclination angle with respect to the axial direction than the first angle and the third angle.

In one aspect, the sliding member has a circular outer shape or a polygonal outer shape, and at least a portion of an outer peripheral surface thereof is arranged to abut against an inner surface of the groove portion.

In one aspect, the groove portion includes a first supporting gear formed in an inner surface thereof against which the sliding member abuts, and the sliding member includes a second supporting gear that is engageable with the first gear.

In one aspect, the transmission member includes a first transmission gear that is provided at the sliding member and a second transmission gear that is provided at the moving member and is engageable with the first transmission gear.

In another embodiment, a medical apparatus includes the bending operating member discussed above; and an elongated member that has flexibility and has a lumen allowing a fluid to circulate therethrough formed therein, the bending operating member being configured to perform a bending operation on the elongated member.

In one aspect, the medical apparatus further includes a balloon that is arranged on a distal portion side of the elongated member, is expanded and deformed by inflow of a fluid, and is contracted and deformed by discharge of the fluid.

According to one embodiment of the present invention, a predetermined region of the elongated member can be bent with a simple operation of rotating the rotating member provided at the bending operating member around the axis of the elongated member. Additionally, even when the bending operating member is used after being attached to a medical apparatus including the elongated member serving as a target to be bending-operated, the bending operating member can be assembled without making the rotating member for driving a bending operation protrude to a side portion of the medical apparatus. Therefore, it is possible to prevent the rotating member from being carelessly touched by fingers which causes a malfunction when the medical apparatus is used. Hence, it is possible to provide a medical apparatus that has the function of bending the elongated member, and has improved operativity and convenience during use.

According to one aspect of the invention, since the sliding member is slidingly moved in the inclined groove portion provided in the converting part by rotating the rotating member, and the movement of the sliding member is transmitted to the moving member for driving the pulling movement of the pulling member, the rotation of the rotating member can be converted into the straight movement of the moving member, and thus, the rotation of the rotating member can be efficiently converted into the pulling movement of the pulling member. Also, the bending amount of the elongated member is determined according to a distance by which the sliding member moves in the inclined groove portion. Therefore, compared to a case where a configuration in which the sliding member is simply moved straight along the axial direction is adopted, the traveling distance of the sliding member in the axial direction can be increased, and the bending amount of the elongated member can be increased without enlarging the bending operating member.

According to one aspect of the invention, the traveling distance of the sliding member is adjusted according to the angles of the respective inclination portions of the groove portion. In an inclination portion with a gentle inclination, the bending amount is adjusted to be low according to the rotational amount of the rotating member. In an inclination portion with a steep inclination, the bending amount is adjusted to be large according to the rotational amount of the rotating member. For this reason, the degree of freedom of the bending operation of the elongated member by the bending operating member can be improved, and a medical apparatus that is more user-friendly can be provided.

According to one aspect of the invention, when the sliding member moves in the first inclination portion and the third inclination portion, the bending amount of the elongated member is adjusted to be smaller than when the sliding member moves in the second inclination portion. For this reason, the bending amount can be finely adjusted in the first inclination portion and the third inclination portion, and a bending operation with a predetermined bending amount can be rapidly performed in the second inclination portion.

According to one aspect of the invention, when the sliding member includes a circular outer shape, the frictional resistance between the sliding member and the inner surface of the groove portion is reduced. Therefore, the sliding member can be smoothly moved and the rotational operation of the rotating member is easily performed. Additionally, when the sliding member includes a polygonal outer shape, the frictional resistance between the sliding member and the groove portion becomes large. Therefore, the movement of the sliding member can be limited, and fine adjustment of the bending amount of the elongated member is easily performed.

According to one aspect of the invention, the traveling distance of the sliding member in the groove portion can be simply adjusted by the first supporting gear provided at the groove portion and the second supporting gear provided at the sliding member. Therefore, it is possible to more precisely adjust the bending amount of the elongated member.

According to one aspect of the invention, since the movement of the sliding member can be efficiently transmitted to the moving member by the first transmission gear and the second transmission gear of the transmission member, the followability of the bending operation of the elongated member accompanying the rotation of the rotating member can be improved.

According to one embodiment of the invention, the bending operating member, and the medical apparatus including the elongated member in which a bending operation is allowed by the bending operating member can be provided. Additionally, according to the medical apparatus, it is possible to perform medical treatments such as supply of a fluid into a living body or suction of various fluids in the living body, via the lumen provided in the elongated member.

According to one aspect of the invention, the balloon catheter including the elongated member capable of performing a bending operation and the balloon capable of being expanded and contracted can be provided.

BRIEF DESCRIPTION OF DRAWINGS

FIG. 2A is a partial cross-sectional view along an axial direction of the medical apparatus, and FIG. 2B is an enlarged cross-sectional view showing a distal portion of an elongated member of the medical apparatus.

FIG. 3A is an enlarged view showing the distal portion of the elongated member before and after the bending operation, and FIG. 3B is a simplified view showing the movement path of a sliding member that moves along a groove portion formed in a rotating member.

FIG. 4A is a view showing a modification example in which the sliding member is formed in a circular shape, FIG. 4B is a view showing a modification example in which a gear is formed in the groove portion and the sliding member, and FIG. 4C is a view showing a modification example in which the groove portion is formed so as to incline at a constant angle.

FIG. 6A is a partial cross-sectional view along an axial direction of the medical apparatus, and FIG. 6B is an enlarged cross-sectional view showing a distal portion of an elongated member of the medical apparatus.

DETAILED DESCRIPTION

Hereinafter, the embodiments of the invention will be described with reference to the drawings. In addition, for convenience of description, dimensional scales of the drawings may be exaggerated and be different from actual scales.

First Embodiment

Figure 1:
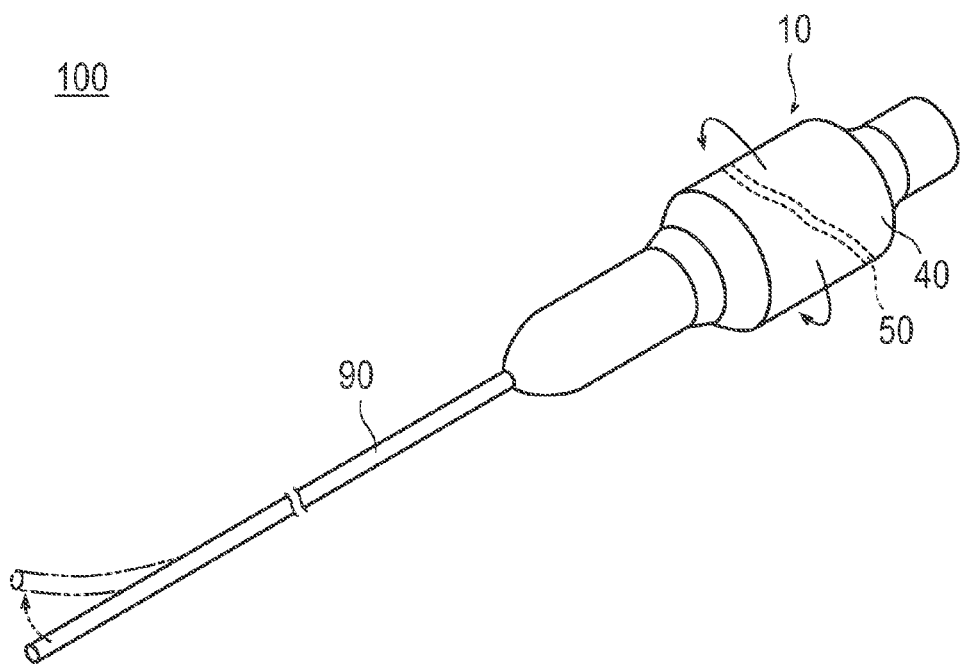
FIG. 1 is a comprehensive perspective view of a medical apparatus related to a first embodiment of the invention.

FIG. 1 is a perspective view showing the overall configuration of a medical apparatus related to the present embodiment, FIG. 2 is a partial cross-sectional view provided for description of respective components of the medical apparatus related to the present embodiment, and FIG. 3 is a view provided for description of the operation of the medical apparatus related to the present embodiment.

Figure 2A:
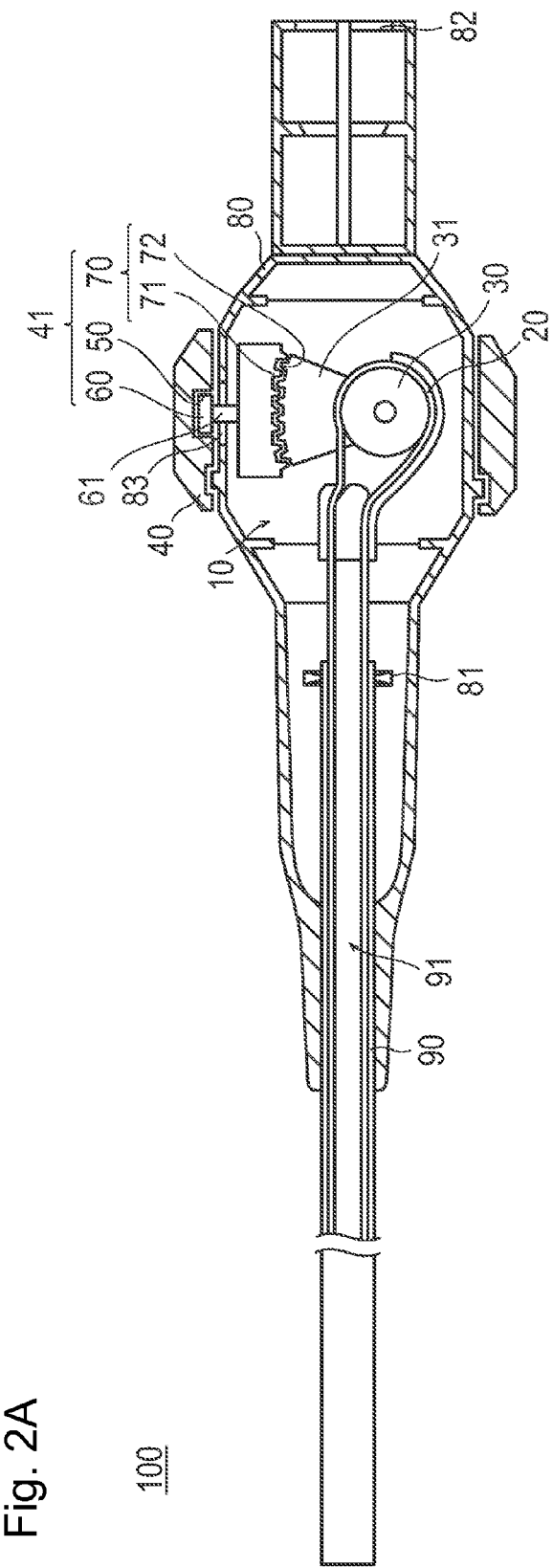
FIGS. 2A and 2B are views for describing respective components of the medical apparatus related to the first embodiment.
Figure 2B:
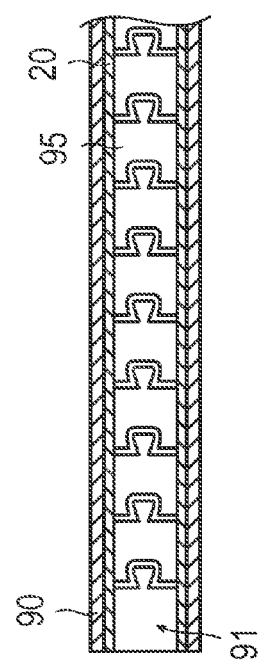
Figure 3A:
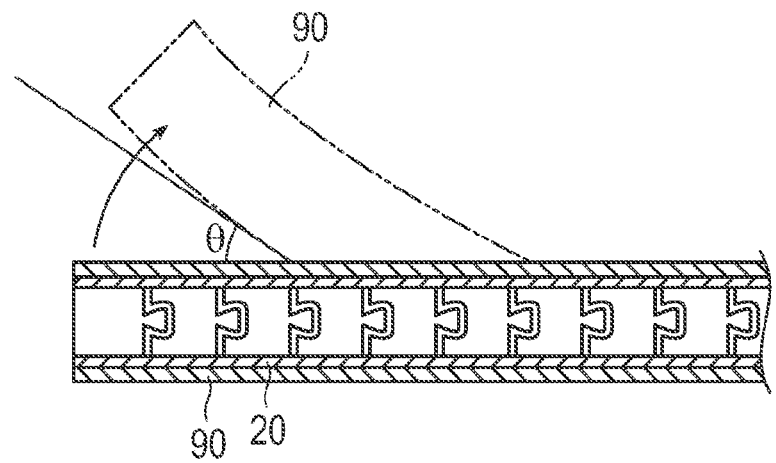
FIGS. 3A and 3B are views for describing a bending operation of the medical apparatus related to the first embodiment.

Generally stated with reference to FIG. 1 and FIGS. 2A and 2B, a medical apparatus 100 according to the present embodiment has an elongated member 90 having flexibility, and a bending operating member 10 capable of performing the bending operation of bending the elongated member 90 in a direction intersecting an axial direction.

The elongated member 90 includes a lumen 91 that enables a fluid to be circulated therethrough (refer to FIG. 2B), and is a medical member provided so as to enable various medical devices to be introduced via the lumen or enable fluids to be circulated via the lumen. On the other hand, the bending operating member 10 is used after being assembled to the elongated member 90, and is used for the bending operation of a predetermined region of the elongated member 90. The medical apparatus 100 can be used in order to guide, for example, medical treatment tools such as an endoscope, various imaging means, and a balloon catheter to a predetermined site in a living body.

Hereinafter, the respective components of the medical apparatus 100 will be described in detail. In the description of the specification, a distal side (left side of FIG. 2A) to which the elongated member 90 extends is referred to as a distal side of the medical apparatus 100, and a side where respective components of the bending operating member 10 are arranged is referred to as a proximal side (right side of FIG. 2A) of the medical apparatus 100. Additionally, the axial direction of the elongated member 90 means a direction in which the elongated member 90 extends, that is, a left-and-right direction of FIG. 2A.

As shown in FIG. 2B, the elongated member 90 is not particularly limited in structure if the elongated member has flexibility. In the present embodiment, a tubular member is used. The tubular member is bendable via a plurality of bending pieces 95 that are juxtaposed in the axial direction. A lumen 91 is formed in the tubular member. The bendable region of the elongated member 90 extends for a predetermined length from the distal side of the elongated member 90 towards the proximal side. However, the length is not particularly limited, and can be set according to the application of the medical apparatus 100.

Materials that constitute the elongated member 90 may include, for example, polyesters such as polyvinyl chloride, polyethylene, polypropylene, cyclic polyolefin, polystyrene, poly(4-methylpentene-1), polycarbonate, acrylate resin, an acrylonitrile-butadiene-styrene copolymer, polyethylene terephthalate, and polyethylenenaphthalate, various soft or rigid resins, such as a butadiene-styrene copolymer and polyamide (for example, nylon 6, nylon 6·6, nylon 6·10, nylon 12), various rubber materials such as natural rubber, butyl rubber, isoprene rubber, butadiene rubber, styrene-butadiene rubber, and silicone rubber, various thermoplastic elastomers such as polyurethane-based, polyester-based, polyamide-based, olefin-based, and styrene-based thermoplastic elastomers, various metallic materials such as stainless steel, aluminum, copper, and a copper-based alloy, various kinds of glass, various ceramics such as alumina and silica.

As shown in FIG. 2A, the bending operating member 10 has a pulling member 20 that has at least a portion connected to a distal portion side of the elongated member 90 and is pulled in the axial direction of the elongated member 90 to thereby bend the elongated member 90, a moving member 30 that is connected to the pulling member 20 on a proximal portion side of the elongated member 90 and moves in the axial direction of the elongated member 90 to pull the pulling member 20, a rotating member 40 that is connected to the moving member 30 and is rotatable around the axis of the elongated member 90, and a converting part 41 that converts the rotation of the rotating member 40 into the movement of the moving member 30.

The bending operating member 10 can be made to include a body cover portion 80 to which the above respective constituent members are attachable. The body cover portion 80 is provided so as to be capable of receiving the pulling member 20, the moving member 30, the converting part 41, and the like. The rotating member 40 can be rotatably attached to an external surface of the body cover portion 80. A supporting member 81 for preventing loosening of the pulling member 20 or coming-off of the elongated member 90 can also be provided inside the body cover portion 80. Additionally, an opening portion 82 is provided at a proximal end of the body cover portion 80, and an endoscope, various imaging means, medical treatment tools, or the like can be introduced into the lumen 91 of the elongated member 90 via the opening portion 82. The body cover portion 80 can be constituted by, for example, a rigid plastic material or the like.

The pulling member 20 can be constituted by, for example, a corded member having flexibility, a plate-shaped member having flexibility, or the like. Although materials that constitute the pulling member 20 may include, for example, nickel titanium or the like, the materials are not particularly limited. Materials capable of transmitting a predetermined force to the elongated member 90 via the pulling member 20 can be appropriately selected. Additionally, as connection forms of the pulling member 20 and the elongated member 90, methods, such as fusing or welding, may be adopted according to the materials of both the members, or a mechanical connection method of anchoring the members through fitting or the like may be adopted. In the medical apparatus 100, a connection form in which the pulling member 20 is fitted and anchored to an inner surface of the elongated member 90 is adopted.

The moving member 30, which is a member for driving the pulling movement of the pulling member 20, can be constituted by, for example, a pulley around which a proximal portion of the pulling member 20 is wound as shown in the drawing.

The rotating member 40 is formed in a substantially tubular shape, and is attached to an external surface of the body cover portion 80 by fitting. The rotating member 40 may constitute a gripping portion to be gripped by a user when the medical apparatus 100 is used in a state where the rotating member is attached to the body cover portion 80. As shown in FIG. 1, as a user rotates the rotating member 40, the bending operation of bending a predetermined region of the elongated member 90, for example, a predetermined range of the distal portion, as shown, can be performed. Additionally, the rotating member 40 is provided with a groove portion 50 where a sliding member 60, to be described below, is arranged.

Figure 3B:
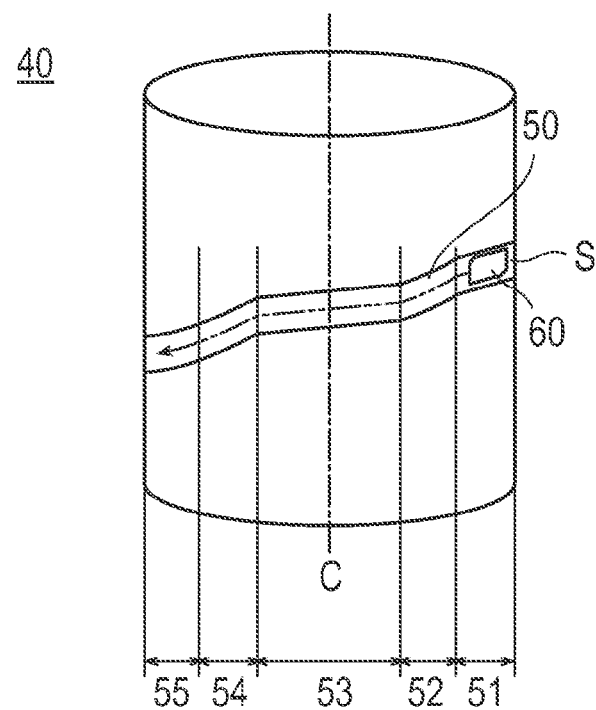

As shown in FIGS. 2 and 3, the converting part 41 of the bending operating member 10 can be configured so as to have the groove portion 50 that is formed in the rotating member 40 and extends so as to incline in the axial direction (an axis C shown in FIG. 3B) of the elongated member 90, the sliding member 60 that is arranged at the groove portion 50 and is slidingly movable along the groove portion 50 accompanying the rotation of the rotating member 40, and a transmission member 70 that transmits the movement of the sliding member 60 to the moving member 30.

The groove portion 50 is formed in an inner surface of the rotating member 40, and the sliding member 60 can be arranged within the groove portion 50. The sliding member 60 is arranged at an initial position S in a state before the elongated member 90 is bent. The elongated member 90 is bent so that a bending angle θ (see FIG. 3A) becomes continuously larger as the sliding member 60 moves along the groove portion 50 from the initial position S toward the proximal side (lower side in FIG. 3B). When the initial position S is set at the end portion of the groove portion 50 on the distal side as shown in the drawing, the elongated member 90 is bent in one direction as the sliding member 60 moves to the proximal side. However, the elongated member 90 can also be configured so as to be bendable in two directions, for example, by setting the initial position S at a middle position between the end portion of the groove portion 50 on the distal side and the end portion of the groove portion 50 on the proximal side. Additionally, a configuration may also be adopted in which the initial position S is set at the end portion of the groove portion 50 on the proximal side and the elongated member 90 is bent by moving the sliding member 60 from the end portion of the groove portion 50 on the proximal side to the end portion of the groove portion on the distal side.

The sliding member 60 is connected to the moving member 30 via a supporting member 61. An upper end portion side of the supporting member 61 can be located on the outside of the body cover portion 80 via an opening portion 83 provided in the body cover portion 80. The sliding member 60, as shown in the drawing, can be configured so as to have, for example, a polygonal outer shape, and a portion of an outer peripheral surface (flat region) of the sliding member is arranged so as to abut against an inner surface of the groove portion 50.

The transmission member 70 can be configured so as to include a first transmission gear 71 provided at the sliding member 60, and a second transmission gear 72 that is provided at the moving member 30 and engageable with the first transmission gear 71. As shown in FIG. 2A, the first transmission gear 71 can be provided, for example, at the supporting member 61 attached to the sliding member 60, and the second transmission gear 72 can be provided at an arm member 31 that extends from the moving member 30 to the supporting member 61.

Next, a mechanism in which the rotation of the rotating member 40 is converted into the movement of the moving member 30 and the pulling movement of the pulling member 20 and thus the bending operation of the elongated member 90 is driven will be described.

If a user who performs a bending operation rotates the rotating member 40, the sliding member 60 moves along the groove portion 50 according to this rotation. The movement of the sliding member 60 is transmitted to the moving member 30 via the transmission member 70 including the first transmission gear 71 and the second transmission gear 72. The moving member 30 constituted by the pulley is rotated to pull the pulling member 20 wound around the moving member 30 to the proximal side if the movement of the sliding member 60 is transmitted thereto. By pulling the pulling member 20, a predetermined region of the elongated member 90 on the distal side to which the pulling member 20 is connected is pulled and bent. In this way, the elongated member 90 can be bent by the simple operation of rotating the rotating member 40.

In the mechanism that converts the rotation of the rotating member 40 into the bending operation of the elongated member 90 by using the sliding member 60 and the obliquely formed groove portion 50, the bending amount of the elongated member 90 is determined according to a distance at which the sliding member 60 moves in the groove portion 50. For this reason, if the angle of the groove portion 50 is gentle (small) when the sliding member 60 moves in the groove portion 50, the traveling distance of the sliding member 60 according to the amount of user's proximal rotation also becomes small and the bending amount of the elongated member 90 becomes small. In contrast, if the angle of the groove portion 50 is steep (large), even when a rotational operation is performed with the same degree of rotational amount as in a case where the angle of the groove portion 50 is gentle, the traveling distance of the sliding member 60 becomes relatively large and the bending amount of the elongated member 90 becomes large. In this way, the relative variation of the bending amount of the elongated member 90 according to a user's proximal operational amount can be adjusted by adjusting the angle of the groove portion 50 formed in the rotating member 40 with respect to the axial direction.

Here, the groove portion 50 formed in the rotating member 40 of the bending operating member 10 is provided with a first inclination portion 51 that inclines at a first angle and a second inclination portion 52 that inclines at a second angle different from the first angle. The first angle of the first inclination portion 51 is set so as to have a gentler inclination angle with respect to the axial direction than the second angle of the second inclination portion 52. Accordingly, even if a user rotates the rotating member 40 with the same rotational amount, the bending amount of the elongated member 90 according to the traveling distance of the sliding member 60 becomes relatively small in the first inclination portion 51, and the bending amount of the elongated member 90 according to the traveling distance of the sliding member 60 becomes relatively large in the second inclination portion 52. For example, when various medical actions are performed using the elongated member 90, the work of adjusting the approach angle of the elongated member 90 according to a site to be treated may be performed. In this case, if the first inclination portion 51 is provided to correspond to an angle range (bending amount) where it is required to finely adjust the bending angle θ and the second inclination portion 52 is provided to correspond to a region where an angle is relatively largely changed and angle adjustment is rapidly performed, the bending operating member 10 and the medical apparatus 100 into which the bending operating member 10 is assembled can be made more user-friendly.

In the bending operating member 10, the groove portion 50 is also formed with a third inclination portion 53. Also, the second inclination portion 52 is formed so as to have an inclination angle at which the second inclination portion 52 inclines more largely in the axial direction than the first inclination portion 51 and the third inclination portion 53. The first inclination portion 51, the second inclination portion 52, and the third inclination portion 53 are continuously formed from the distal side toward the proximal side, respectively. The second inclination portion 52 is formed so as to be located further toward the proximal side (lower side in FIG. 3B) than the first inclination portion 51, and the third inclination portion 53 is formed so as to be located further toward the proximal side than the second inclination portion 52.

Additionally, the groove portion 50, as shown in the drawing, may be formed with a fourth inclination portion 54 and a fifth inclination portion 55 together with the first inclination portion 51, the second inclination portion 52, and the third inclination portion 53. The fourth inclination portion 54 can be formed, for example, so as to extend from the third inclination portion 53 to the proximal side, and the fifth inclination portion 55 can be formed, for example, so as to extend from the fourth inclination portion 54 to the proximal side.

Although the magnitude relationship of the inclination angles of the respective inclination portions is not particularly limited, for example, the inclination angles of the second inclination portion 52 and the fourth inclination portion 54 can be set to be larger than the other inclination portions, and the inclination angles of the first inclination portion 51, the third inclination portion 53, and the fifth inclination portion 55 can be set to be the same degree of magnitude, respectively. Additionally, for example, the range of the bending angle θ at which the elongated member 90 is bent when the sliding member 60 moves in the first inclination portion 51 can be set to be 0 to 35 degrees, the range of the bending angle θ at which the elongated member 90 is bent when the sliding member 60 moves in the third inclination portion 53 can be set to be 65 to 75 degrees, and the range of the bending angle θ at which the elongated member 90 is bent when the sliding member 60 moves in the fifth inclination portion 55 can be set to be 85 to 115 degrees. This is based on the following reasons.

For example, when the medical apparatus 100 into which the bending operating member 10 is assembled is used for the treatment of sinusitis, known as a disease related to the ears and nose, the work of guiding the distal portion of the elongated member 90 to a site where a stenosis site causing sinusitis is formed and introducing various medical devices via the elongated member 90 is performed. In this case, sites serving targets to be treated mainly include a sphenoid sinus, a frontal sinus, and a maxillary sinus. When the medical apparatus 100 is inserted from the nostril of an external nose, in order to smoothly guide the elongated member 90 to the sphenoid sinus, it is preferable to advance the medical apparatus at a bending angle of about 0 to 30 degrees with respect to an insertion direction. Additionally, regarding the frontal sinus, it is preferable to advance the medical apparatus at a bending angle of about 70 degrees. Additionally, regarding the maxillary sinus, it is preferable to advance the medical apparatus at a bending angle of about 90 to 110 degrees. Accordingly, it may be preferable to perform a design such that the bending angles as described above are allocated to the first inclination portion 51, the third inclination portion 53, and the fifth inclination portion 55, respectively, so that the bending angle of the elongated member 90 can be finely adjusted when being guided to the respective sites to be treated.

Additionally, it is also possible to adopt, for example, a form in which, in the relationship between the first inclination portion 51, the third inclination portion 53, and the fifth inclination portion 55, the inclination angle of the first inclination portion 51 located on the distal side is made largest and inclination angles are made small in order of the inclination angle of the third inclination portion 53 and the inclination angle of the fifth inclination portion 53 and in the relationship between the second inclination portion 52 and the fifth inclination portion 55, the inclination angle of the second inclination portion 52 located on the distal side is made larger than the inclination angle of the fifth inclination portion 55. In this case, there are the following advantages.

If the operation of rotating the rotating member 40 in a given direction to bend the distal portion of the elongated member 90 so that the bending angle θ becomes continuously large is performed, a starting point of the bending of the elongated member 90 moves gradually from the distal side of the elongated member 90 to the proximal side. When the starting point of the bending is located on the distal side of the elongated member 90, the bending amount of the elongated member 90 is suppressed to a small degree. On the other hand, if the starting point of the bending moves to the proximal side, the bending amount becomes larger than when the starting point of the bending is located on the distal side irrespective of whether a user rotates the rotating member 40 with a constant amount. In this case, if the inclination angles of the respective inclination portions of the groove portion 50 are made larger on the distal side than on the proximal side, a difference in the bending amount that may be caused depending on the position of the starting point of the bending of the elongated member 90 can be suppressed to be low, and the bending amount of the elongated member 90 can be more precisely adjusted with a proximal operational feeling.

Additionally, although the form in which the inclination angles changes gradually depending on the plurality of inclination portions is shown, the form of the groove portion 50 is not limited to such a form. For example, it is also possible to adopt a form in which the inclination angles become continuously small from the distal side of the groove portion 50 to the proximal side, a form in which a constant inclination angle is given as in a modification example to be described below, or the like.

As described above, according to the bending operating member 10 related to the present embodiment, the predetermined region of the elongated member 90 can be bent with the simple operation of rotating the rotating member 40 provided at the bending operating member 10 around the axis of the elongated member 90. Additionally, even when the bending operating member 10 is used after being attached to the medical apparatus 100 including the elongated member 90 serving as a target to be bending-operated, the bending operating member 10 can be assembled without making the rotating member 40 for driving a bending operation protrude to the side portion side of the medical apparatus 100. Therefore, it is possible to prevent the rotating member 40 from being carelessly touched by fingers which causes a malfunction when the medical apparatus 100 is used. Hence, it is possible to provide the medical apparatus 100 that has the function of bending the elongated member 90, has improved operativity, and has excellent convenience.

Additionally, since the sliding member 60 is slidingly moved in the inclined groove portion 50 provided in the converting part 41 by rotating the rotating member 40, and the movement of the sliding member 60 is transmitted to the moving member 30 for driving the pulling movement of the pulling member 20, the rotation of the rotating member 40 can be converted into the straight movement of the moving member 30, and thus, the rotation of the rotating member 40 can be efficiently converted into the pulling movement of the pulling member 20. Also, the bending amount of the elongated member 90 is determined according to a distance by which the sliding member 60 moves in the inclined groove portion 50. Therefore, compared to a case where a configuration in which the sliding member 60 is simply moved straight along the axial direction is adopted, the traveling distance of the sliding member 60 in the axial direction can be increased, and the bending amount of the elongated member 90 can be increased without enlarging the bending operating member 10.

Additionally, the traveling distance of the sliding member 60 is adjusted according to the angles of the respective inclination portions of the groove portion 50. In an inclination portion with a gentle inclination, the bending amount is adjusted to be low according to the rotational amount of the rotating member 40. In an inclination portion with a steep inclination, the bending amount is adjusted to be large according to the rotational amount of the rotating member 40.

For this reason, the degree of freedom of the bending operation of the elongated member 90 by the bending operating member 10 can be improved, and the medical apparatus 100 that is more user-friendly can be provided.

Additionally, when the sliding member 60 moves in the first inclination portion 51 and the third inclination portion 53, the bending amount of the elongated member 90 is adjusted to be smaller than when the sliding member moves in the second inclination portion 52. For this reason, the bending amount can be finely adjusted in the first inclination portion 51 and the third inclination portion 53, and a bending operation with a predetermined bending amount can be rapidly performed in the second inclination portion 52.

Additionally, since the sliding member 60 includes a polygonal outer shape, the frictional resistance between the sliding member 60 and the groove portion 50 becomes large. As a result, the movement of the sliding member 60 can be limited, and fine adjustment of the bending amount of the elongated member 90 is easily performed.

Additionally, since the movement of the sliding member 60 can be efficiently transmitted to the moving member 30 by the first transmission gear 71 and the second transmission gear 72 of the transmission member 70, the followability of the bending operation of the elongated member 90 accompanying the rotation of the rotating member 40 can be improved.

Modification Examples

Next, modification examples of the above-described embodiment will be described.

Figure 4A:
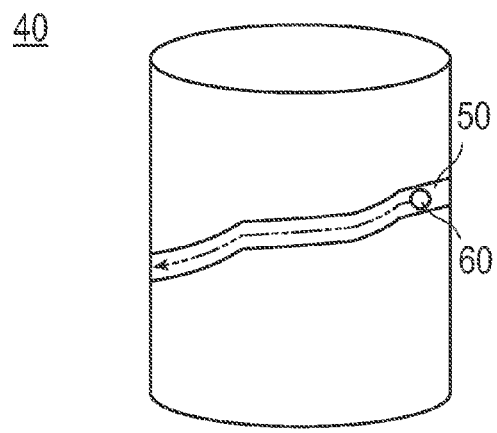
FIGS. 4A to 4C are views showing modification examples of the groove portion formed in the rotating member and the sliding member.
Figure 4B:
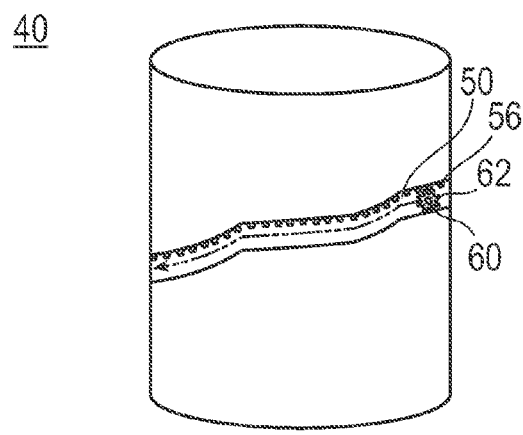
Figure 4C:
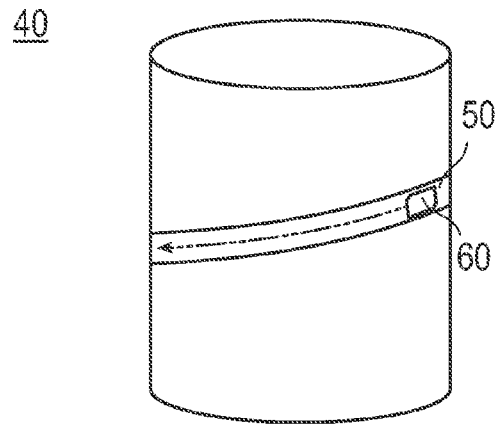

FIGS. 4A to 4C are views showing modification examples of the sliding member 60 and the groove portion 50.

As shown in FIG. 4A, the sliding member 60 can be configured so as to have, for example, a circular outer shape such that at least a portion of an outer peripheral surface thereof is arranged to abut against the inner surface of the groove portion 50. If the sliding member 60 is configured in this way, the frictional resistance between the sliding member 60 and the inner surface of the groove portion 50 is reduced. Therefore, the sliding member 60 can be smoothly moved and the rotational operation of the rotating member 40 is easily performed.

Additionally, as shown in FIG. 4B, for example, the groove portion 50 may be provided with a first supporting gear 56 formed in the inner surface thereof against which the sliding member 60 abuts, and the sliding member 60 may be provided with a second supporting member 62 that is engageable with the first supporting gear 56. If the groove portion 50 and the sliding member 60 are configured so as to have a gear mechanism in this way, the traveling distance of the sliding member 60 in the groove portion 50 can be simply adjusted. Therefore, it is possible to more precisely adjust the bending amount of the elongated member 90.

Additionally, as shown in FIG. 4C, for example, the groove portion 50 may not be provided with the plurality of inclination portions whose inclination angles are gradually different, but the groove portion 50 may be configured so as to incline at a constant angle from the distal side to the proximal side. Although the function of performing the adjustment of bending amounts made to correspond to the angles of the plurality of inclination portions cannot be added, the bending operating member 10 can be more simply configured.

Figure 5A:
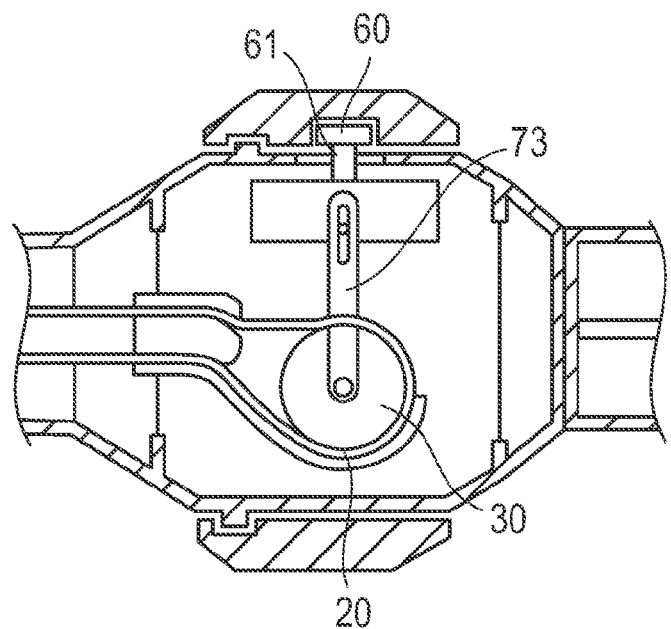
FIGS. 5A and 5B are views respectively showing first and second additional modification examples of a transmission member.
Figure 5B:
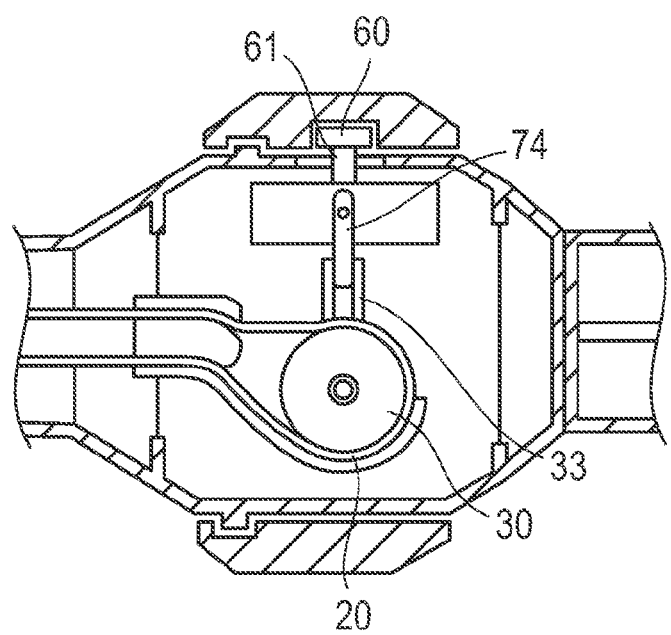

FIGS. 5A and 5B are views showing modification examples of the transmission member 70.

In the above-described embodiment, the configuration in which the transmission member 70 configured so as to have the first transmission gear 71 provided at the sliding member 60 and the second transmission gear 72 provided at the moving member 30 is used has been described. However, the transmission member 70 can be appropriately changed as long as the movement of the sliding member 60 can be transmitted to the moving member 30.

As shown in FIG. 5A, for example, an arm member 73, which is rockably attached to the supporting member 61 attached to the sliding member 60 on one end side thereof and is rotatably journalled to the moving member 30 on the other end side thereof, may be used as the transmission member 70.

Additionally, as shown in FIG. 5B, for example, an arm member 74, which is rotatably journalled to the supporting member 61 attached to the sliding member 60 on one end side thereof and is provided so as to be fittable to a fitting portion 33 connected to the moving member 30 on the other end side thereof, may be used as the transmission member 70.

Even when the transmission members 70 are used as shown in FIGS. 5A and 5B, the movement of the sliding member 60 can be transmitted to the moving member 30 appropriately and the smooth bending operation of the elongated member 90 can be performed.

Second Embodiment

Next, a medical apparatus 200 related to a second embodiment of the invention will be described. In the drawings, the same members as the respective members described in the first embodiment will be designated by the same reference numerals, and a portion of the description thereof will be omitted.

Figure 6A:
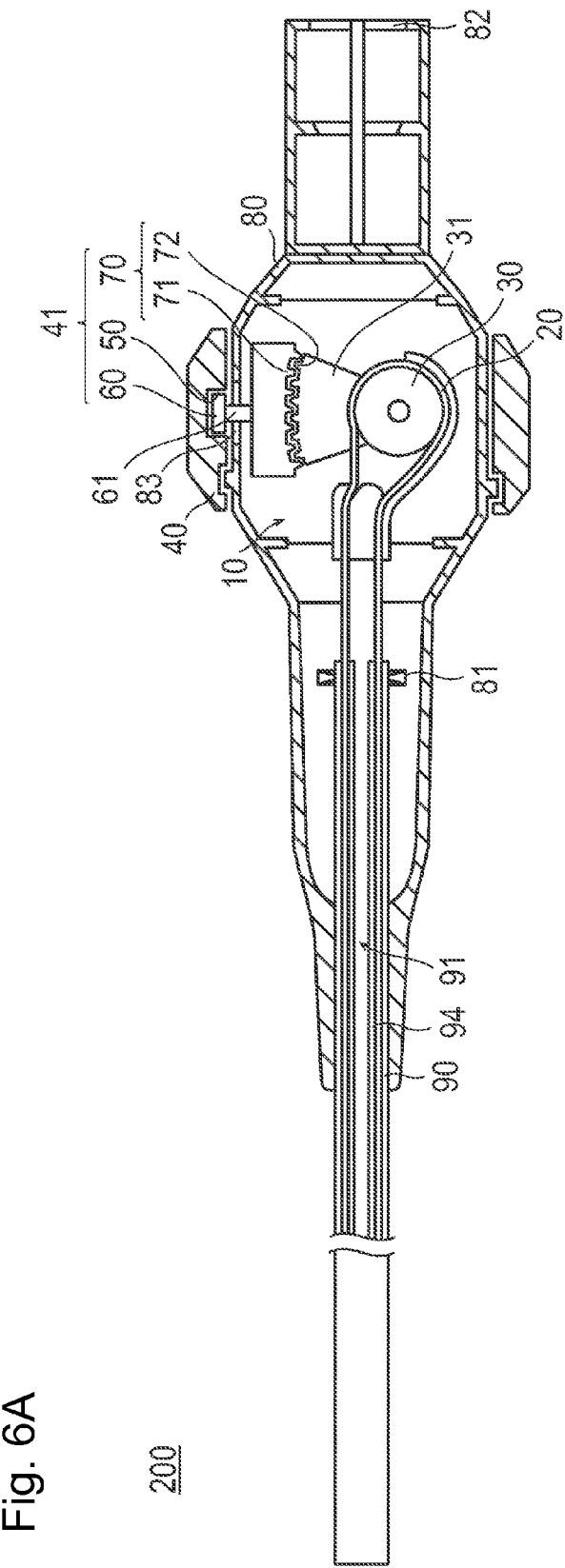
FIGS. 6A and 6B are views for describing respective components of a medical apparatus related to a second embodiment.
Figure 6B:
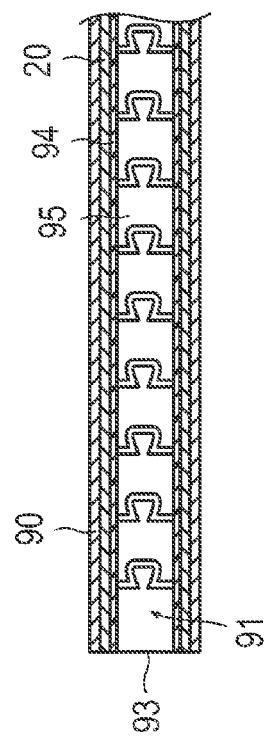

Referring to FIGS. 6A and 6B, a medical apparatus 200 related to the present embodiment is constituted by the medical apparatus 200 for performing suction of various fluids in the living body or supply of various fluids into the living body by the elongated member 90 and the bending operating member 10. A tube 94 for enabling circulation of a fluid is inserted into the lumen 91 of the elongated member 90.

Although the tube 94 is arranged inside the pulling member 20, the arrangement position of the tube is not particularly limited if liquid leaking from the lumen 91 of the elongated member 90 can be prevented. For example, the tube may be arranged between an inner surface of the elongated member 90 and the pulling member 20 or may be arranged so as to cover the elongated member 90. As the tube 94, for example, a well-known tube made of resin can be used.

By connecting a predetermined fluid tube for a fluid (not shown) to a proximal side of the tube 94, the fluid can be supplied to the lumen 91 of the elongated member 90 or the fluid can be suctioned via the lumen 91 of the elongated member 90. In addition, the fluid tube can be pulled out to the outside of the bending operating member 10 via the opening portion 82 provided at the proximal side of the body cover portion 80. In addition to this, the fluid tube can be pulled out to the outside by providing a suitable opening portion in the body cover portion 80. The pulled-out fluid tube can be coupled to other devices such as a fluid pump (not shown).

As described above, according to the medical apparatus 200 related to the present embodiment, it is possible to perform medical treatments such as supply of a fluid into a living body or suction of various fluids in the living body, via the lumen 91 provided in the elongated member 90.

Third Embodiment

Next, a medical apparatus 300 related to a third embodiment of the invention will be described. In the drawings, the same members as the respective members described in the first and second embodiments will be designated by the same reference numerals, and a portion of the description thereof will be omitted.

Figure 7:
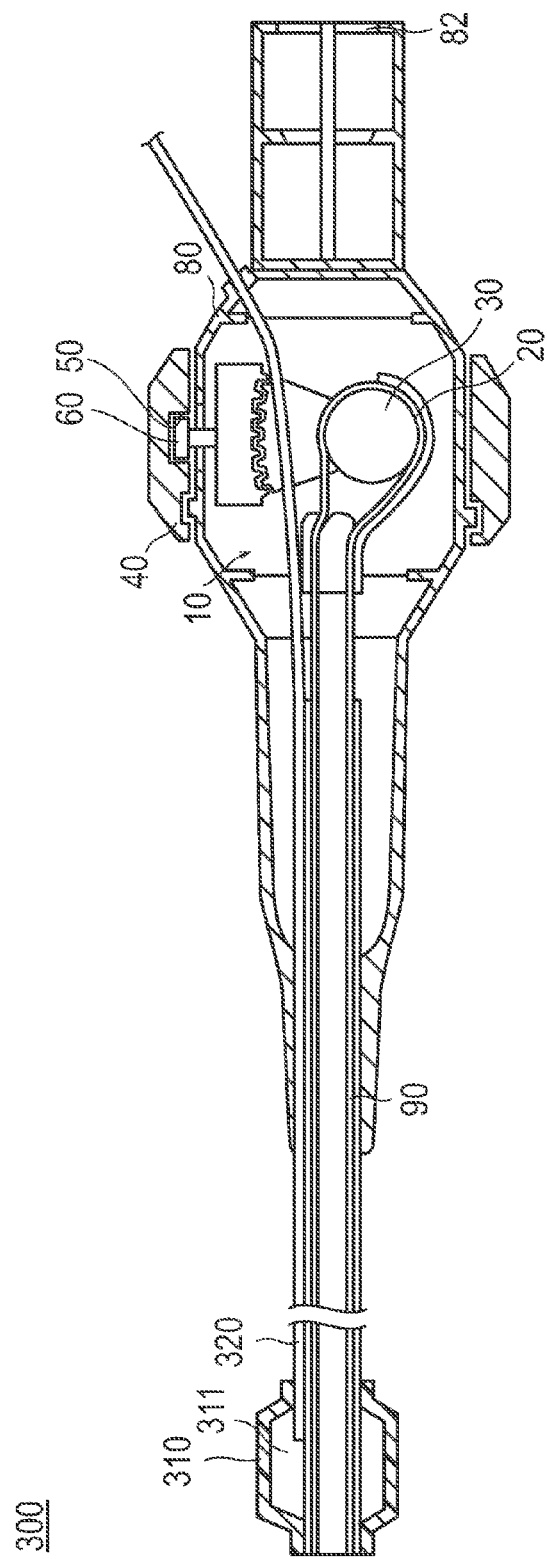
FIG. 7 is a partial cross-sectional view along an axial direction of a medical apparatus related to a third embodiment of the invention.

Referring to FIG. 7, the medical apparatus 300 related to the present embodiment is different from the medical apparatuses 100 and 200 related to the first and second embodiments in that the medical apparatus 300 has a balloon 310 arranged on the distal portion side of the elongated member 90.

The balloon 310 is expanded and deformed by inflow of a fluid, and is contractedly deformed by discharge of the fluid. Although the constituent materials of the balloon 310 are not particularly limited, materials having a certain degree of flexibility are preferable, for example, polyolefins such as polyethylene, polypropylene, and ethylene propylene copolymers are used. Additionally, fluids used for the expansion of the balloon may be gases or liquids, and may include, for example, gases such as helium gas, $CO_2$ gas, and $O_2$ gas or liquids such as a physiological salt solution.

The balloon 310 is attached to an outer peripheral surface of the elongated member 90 by well-known methods such as welding and fusing, and an internal space 311 that allows a fluid to flow thereinto is partitioned between an inner surface of the balloon 310 and an external surface of the elongated member 90. Additionally, a predetermined fluid tube 320 is connected so as to face the internal space, and supply and discharge of a fluid can be performed via the fluid tube 320. The fluid tube 300 can be led out from a predetermined region on the proximal side of the body cover portion 80 through the inside of the body cover portion 80. In order to reliably prevent liquid leaking from the internal space 311 of the balloon 310, the elongated member 90 may be covered with a predetermined resin tube or the like.

As shown in the present embodiment, even when the bending operating member 10 is assembled into a balloon catheter, the bending operation of the elongated member 90 can be simply performed, and a user-friendly medical apparatus 300 can be provided.

Although the bending operating member and medical apparatus related to the invention have been described above on the basis of the embodiments, the invention is not limited only to the configurations shown in the respective embodiments and the modification examples, and can be variously modified on the basis of the definitions of the claims. Additionally, the respective embodiments and the respective modification examples may be combined, respectively, or the bending operating member and the medical apparatus may be independently constituted according to respective forms.

Medical apparatuses to which the bending operating member is applied are not limited only to a medical apparatus guiding various medical devices to respective regions of a living body and a medical apparatus or a balloon catheter aimed at performing supply and discharge of a fluid, and can be appropriately changed as long as the medical apparatuses aim at performing the bending operation of the elongated member. For example, the invention can also be applied to a catheter device for delivery of medicine, or the like.

What is claimed is:

1. A bending operating member for performing a bending operation on an elongated member having flexibility in a direction intersecting an axial direction of the elongated member, the bending operating member comprising:
a pulling member, at least a portion of the pulling member being configured to be connected to a distal portion of the elongated member such that, when said pulling member is pulled in the axial direction of the elongated member, the pulling member causes the elongated member to bend;
a moving member that is connected to the pulling member, the moving member being configured to move so as to pull the pulling member in the axial direction of the elongated member;
a rotating member that is operatively connected to the moving member and is rotatable around a longitudinal axis of the elongated member; and
a converting part that converts rotation of the rotating member into movement of the moving member,
wherein a groove portion is formed in the rotating member and extends so as to incline in the axial direction of the elongated member,
wherein the converting part includes a sliding member that is arranged at the groove portion and is slidingly movable along the groove portion in accordance with the rotation of the rotating member, and a transmission member that transmits the movement of the sliding member to the moving member,
wherein the groove portion includes a first supporting gear formed in an inner surface thereof against which the sliding member abuts, and
wherein the sliding member includes a second supporting gear that is engageable with the first supporting gear.

2. The bending operating member according to claim 1, wherein the groove portion includes at least a first inclination portion that inclines at a first angle and a second inclination portion that inclines at a second angle different from the first angle.

3. The bending operating member according to claim 2, wherein the groove portion further includes a third inclination portion with a third angle different from the second angle, and
the second angle has a larger inclination angle with respect to the axial direction than the first angle and the third angle.

4. The bending operative member according to claim 2, wherein the groove extends continuously from at least a distal end of the first inclination portion to a proximal end of the second inclination portion.

5. The bending operating member according to claim 1, wherein the sliding member has a circular outer shape or a polygonal outer shape, and at least a portion of an outer peripheral surface thereof is arranged to abut against an inner surface of the groove portion.

6. The bending operating member according to claim 1, wherein the transmission member includes a first transmission gear that is connected to the sliding member, and a second transmission gear that is connected to the moving member and is engageable with the first transmission gear.

7. A medical apparatus comprising:
an elongated member having flexibility in a direction intersecting an axial direction of the elongated member, the elongated member having a lumen allowing a fluid to circulate therethrough formed therein; and
a bending operating member for performing a bending operation on an elongated member, the bending operating member comprising:
a pulling member, at least a portion of the pulling member being configured to be connected to a distal portion of the elongated member such that, when said pulling member is pulled in the axial direction of the elongated member, the pulling member causes the elongated member to bend, a moving member that is connected to the pulling member, the moving member being configured to move so as to pull the pulling member in the axial direction of the elongated member, a rotating member that is operatively connected to the moving member and is rotatable around a longitudinal axis of the elongated member, and a converting part that converts rotation of the rotating member into movement of the moving member, wherein a groove portion is formed in the rotating member and extends so as to incline in the axial direction of the elongated member, wherein the converting part includes a sliding member that is arranged at the groove portion and is slidingly movable along the groove portion in accordance with the rotation of the rotating member, and a transmission member that transmits the movement of the sliding member to the moving member, wherein the groove portion includes a first supporting gear formed in an inner surface thereof against which the sliding member abuts, and wherein the sliding member includes a second supporting gear that is engageable with the first supporting gear.

8. The medical apparatus according to claim 7, further comprising:

a balloon arranged on a distal portion side of the elongated member, the balloon being expandable by inflow of fluid to the balloon, and being contractable by discharge of the fluid from the balloon.

9. The bending operative member according to claim 1, wherein the rotating member is rotatably attached to an external surface of a body cover portion.

10. The bending operative member according to claim 1, wherein the moving member is configured to convert the rotation of the rotating member into a pulling movement of the pulling member.

11. The bending operative member according to claim 10, wherein the moving member is configured to convert the rotation of the rotating member into a pulling movement of the pulling member via the converting part.

12. A bending operating member for performing a bending operation on an elongated member having flexibility in a direction intersecting an axial direction of the elongated member, the bending operating member comprising:

a pulling member, at least a portion of the pulling member being configured to be connected to a distal portion of the elongated member such that, when said pulling member is pulled in the axial direction of the elongated member, the pulling member causes the elongated member to bend;

a moving member that is connected to the pulling member, the moving member being configured to move so as to pull the pulling member in the axial direction of the elongated member;

a rotating member that is operatively connected to the moving member and is rotatable around a longitudinal axis of the elongated member; and a converting part that converts rotation of the rotating member into movement of the moving member, wherein a groove portion is formed in the rotating member and extends so as to incline in the axial direction of the elongated member, wherein the converting part includes a sliding member that is arranged at the groove portion and is slidingly movable along the groove portion in accordance with the rotation of the rotating member, and a transmission member that transmits the movement of the sliding member to the moving member, wherein the groove portion includes at least a first inclination portion that inclines at a first angle and a second inclination portion that inclines at a second angle different from the first angle, and wherein the groove extends continuously from at least a distal end of the first inclination portion to a proximal end of the second inclination portion.

13. A medical apparatus comprising:

an elongated member having flexibility in a direction intersecting an axial direction of the elongated member, the elongated member having a lumen allowing a fluid to circulate therethrough formed therein; and a bending operating member for performing a bending operation on an elongated member, the bending operating member comprising:

a pulling member, at least a portion of the pulling member being configured to be connected to a distal portion of the elongated member such that, when said pulling member is pulled in the axial direction of the elongated member, the pulling member causes the elongated member to bend, a moving member that is connected to the pulling member, the moving member being configured to move so as to pull the pulling member in the axial direction of the elongated member, a rotating member that is operatively connected to the moving member and is rotatable around a longitudinal axis of the elongated member, and a converting part that converts rotation of the rotating member into movement of the moving member, wherein a groove portion is formed in the rotating member and extends so as to incline in the axial direction of the elongated member, wherein the converting part includes a sliding member that is arranged at the groove portion and is slidingly movable along the groove portion in accordance with the rotation of the rotating member, and a transmission member that transmits the movement of the sliding member to the moving member, wherein the groove portion includes at least a first inclination portion that inclines at a first angle and a second inclination portion that inclines at a second angle different from the first angle, and wherein the groove extends continuously from at least a distal end of the first inclination portion to a proximal end of the second inclination portion.

14. The medical apparatus according to claim 13, further comprising:

a balloon arranged on a distal portion side of the elongated member, the balloon being expandable by inflow of fluid to the balloon, and being contractable by discharge of the fluid from the balloon.

* * * * *